United States Patent [19]
Kurakake et al.

[11] Patent Number: 5,210,422
[45] Date of Patent: May 11, 1993

[54] SCINTILLATION CAMERA

[75] Inventors: Tadakazu Kurakake; Mikio Igarashi, both of Tokyo, Japan

[73] Assignee: Kabushiki Kaisha Toshiba, Tokyo, Japan

[21] Appl. No.: 835,581

[22] Filed: Feb. 14, 1992

[30] Foreign Application Priority Data

Feb. 14, 1991 [JP] Japan .................. 3-20713

[51] Int. Cl.⁵ .................. G01T 1/20; G21K 1/02
[52] U.S. Cl. .................. 250/363.1; 378/148; 248/181
[58] Field of Search .......... 250/363.02, 363.04, 250/363.05, 363.08, 363.10, 363.03, 505.1; 376/147, 148, 155; 211/41; 248/187, 181

[56] References Cited

U.S. PATENT DOCUMENTS

| 3,982,133 | 9/1976 | Jupa et al. | 378/148 |
| 4,109,155 | 8/1978 | Tschunt et al. | 378/148 |
| 4,129,784 | 12/1978 | Tschunt et al. | 378/148 |
| 5,059,799 | 10/1991 | Kurakake | 250/363.10 |
| 5,097,131 | 3/1992 | Plummer et al. | 250/363.08 |

FOREIGN PATENT DOCUMENTS

| 59-180476 | 10/1984 | Japan | 250/363.10 |
| 2-263185 | 10/1990 | Japan | 378/148 |

Primary Examiner—Constantine Hannaher
Assistant Examiner—Edward J. Glick
Attorney, Agent, or Firm—Oblon, Spivak, McClelland, Maier & Neustadt

[57] ABSTRACT

A scintillation camera includes a plurality of detectors mounted on the camera and arranged to provide an opening for allowing the insertion of an object for examination such as a human being and for radiographing a tomographic image, a plurality of collimators each of which is attached to the front of the corresponding detectors for collimating X-rays radiating from the object for examination, and an exchanger for the collimators, the exchanger including a carrier and a holding device for holding the collimators in a swingable manner in any direction within a certain range by use of a mechanism such as a spherical bearing.

7 Claims, 11 Drawing Sheets

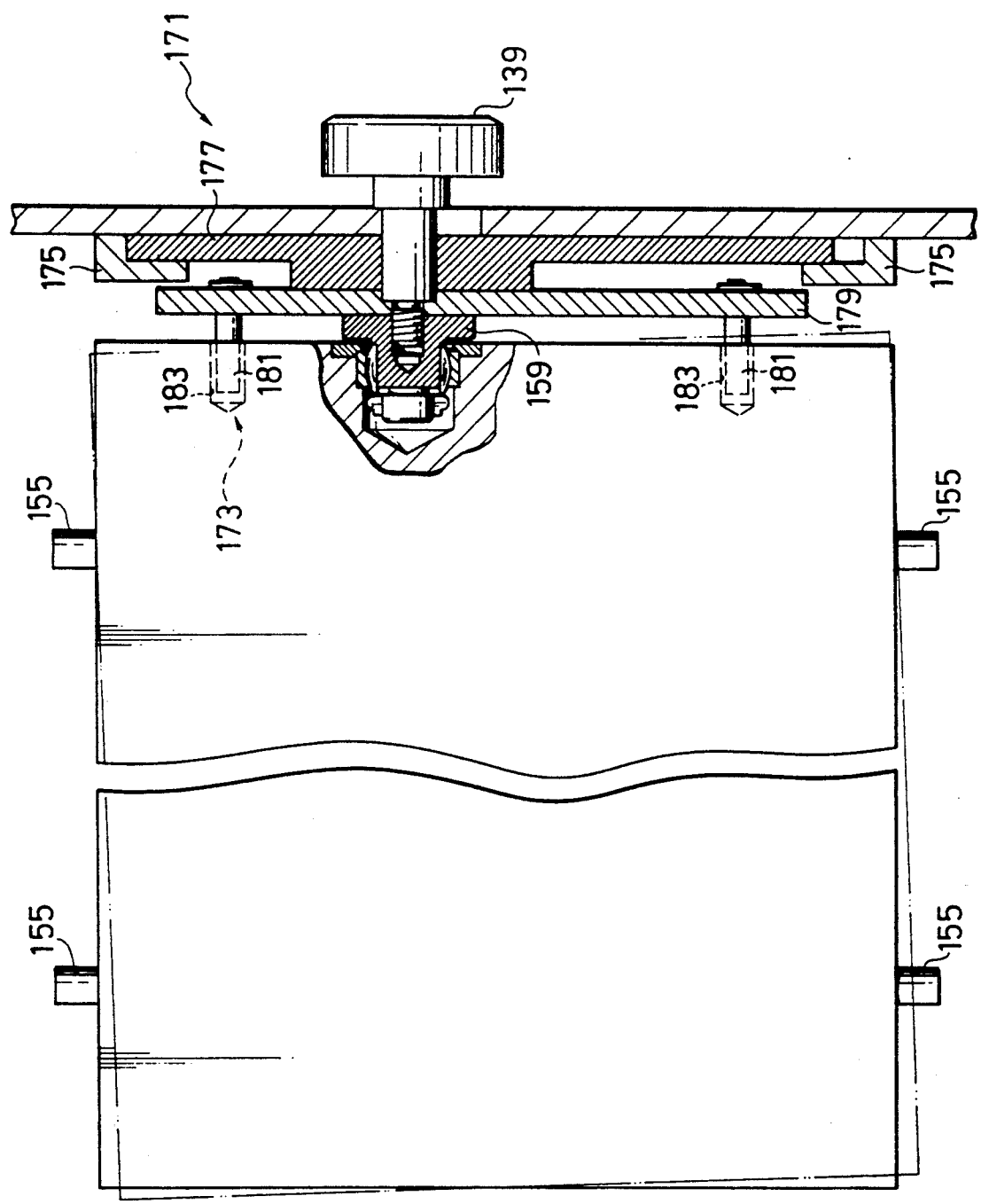

SCINTILLATION CAMERA

BACKGROUND OF THE INVENTION

1. Field of the Invention

The present invention relates to a scintillation camera for radiographing a two dimensional distribution image or a tomographic image in accordance with a radioactive isotope distributed in a body for examination, and more particularly, relates to a scintillation camera including a modified collimator exchanger for changing collimators attached to detectors.

2. Description of the Prior Art

FIG. 1 explains the principle of a conventional scintillation camera. As seen in the figure, gamma rays 11 radiated from the examined body P cause the scintillator 13 to emit fluorescent rays proportional to the energy of the gamma rays. The fluorescent rays are guided to a plurality of photomultiplier tube (PMT) 17 through a light-guide 15 and are changed to electric pulses proportional to the energy level of the fluorescent rays in the PMT. A unit consisting of a scintillator, a light guide and photomultiplier tubes is referred to as a detector 19 hereinafter. The pulses from the detector 19 are processed by a processor 21 to form a tomographic image having a two-dimensional distribution. The tomographic image is displayed on a display unit 23.

In the above device, a collimator 25 is used which only accepts gamma rays which are parallel to its holes and blocks other gamma rays such as a gamma ray entering the collimator openings obliquely. Various kinds of collimators are usable for this purpose. For example, a collimator for high, medium or low energy can be used depending upon the energy of the radioactive isotope. Collimators with different sized openings are used depending upon the required resolution and sensitivity of the images. To be used properly, collimators must be changed according to the radiographic purposes.

A conventional scintillation camera includes a plurality of detectors with collimators attached for parallel processing. A conventional collimator exchanger changes all collimators simultaneously for an efficient exchange. A conventional collimator and holding device is described in U.S. Pat. No. 5,059,799 assigned to the same assignee of the present application. This conventional collimator exchanger comprises a carrier with rails and a holding device for holding collimators. In FIGS. 2A and 2B, the collimator is provided with a screw hole 31, pin holes 33, guide pins 35, a through hole 37 and includes for example, 2000 to 4000 of collimator holes 39.

In FIG. 3, the holding device for holding the collimators comprises a frame 41 secured to a carrier, a first block 43 consisting of upper and lower halves each secured to the frame 41, a second block 45 with a through hole 47 and sliding parts 49 joined to the first block and movable in the Y axis and Z axis directions in the figure, a flat member 51 with a flat surface for attaching the collimator, and an attaching screw 53 for attaching the collimator to the holding section.

In the above-mentioned holding device, the collimators are fully secured to the holding device and are not swingable. Considerable time and trouble are required to attach or detach a plurality of collimators when the detectors are placed in an improper position.

For example, it is sometimes difficult to attach the collimators to an attaching section when the levels of the attaching sections do not agree with the levels of the collimators supported by the holding device, or in which the collimators or the attaching sections are inclined. The problem becomes more serious in a scintillation camera with a plurality of collimators and detectors when they are exchanged simultaneously.

SUMMARY OF THE INVENTION

The present invention has been made in an attempt to solve the above-described various drawbacks, and its object is therefore to provide a scintillation camera including a collimator exchanger capable of more easily changing collimators which are incorrectly positioned.

The above-described object and other features of the present invention may be achieved by providing a scintillation camera comprising:

(a) a plurality of detectors mounted on the camera and arranged to provide an opening for allowing the insertion of an object for examination such as a human body and for radiographing a tomographic image;

(b) a plurality of collimators each attached to the front of the corresponding detector for collimating X-rays radiating from the object for examination;

(c) an exchanger including a carrier and a holding device for holding collimators in a swingable manner in any direction within a specified range.

Preferably, the holding device comprises a spherical bearing for swingably holding collimators, a pin and pinhole set for limiting swingable range.

These and other object, features and advantages of the present invention will be more apparent from the following description of a preferred embodiment in conjunction with the accompanying drawings.

BRIEF DESCRIPTION OF THE DRAWINGS

FIG. 8B is a front sectional view of the holding device shown in FIG. 8A.

FIG. 8C shows the attaching steps for the collimator of the present invention,

DESCRIPTION OF THE PREFERRED EMBODIMENTS

Figure 1:
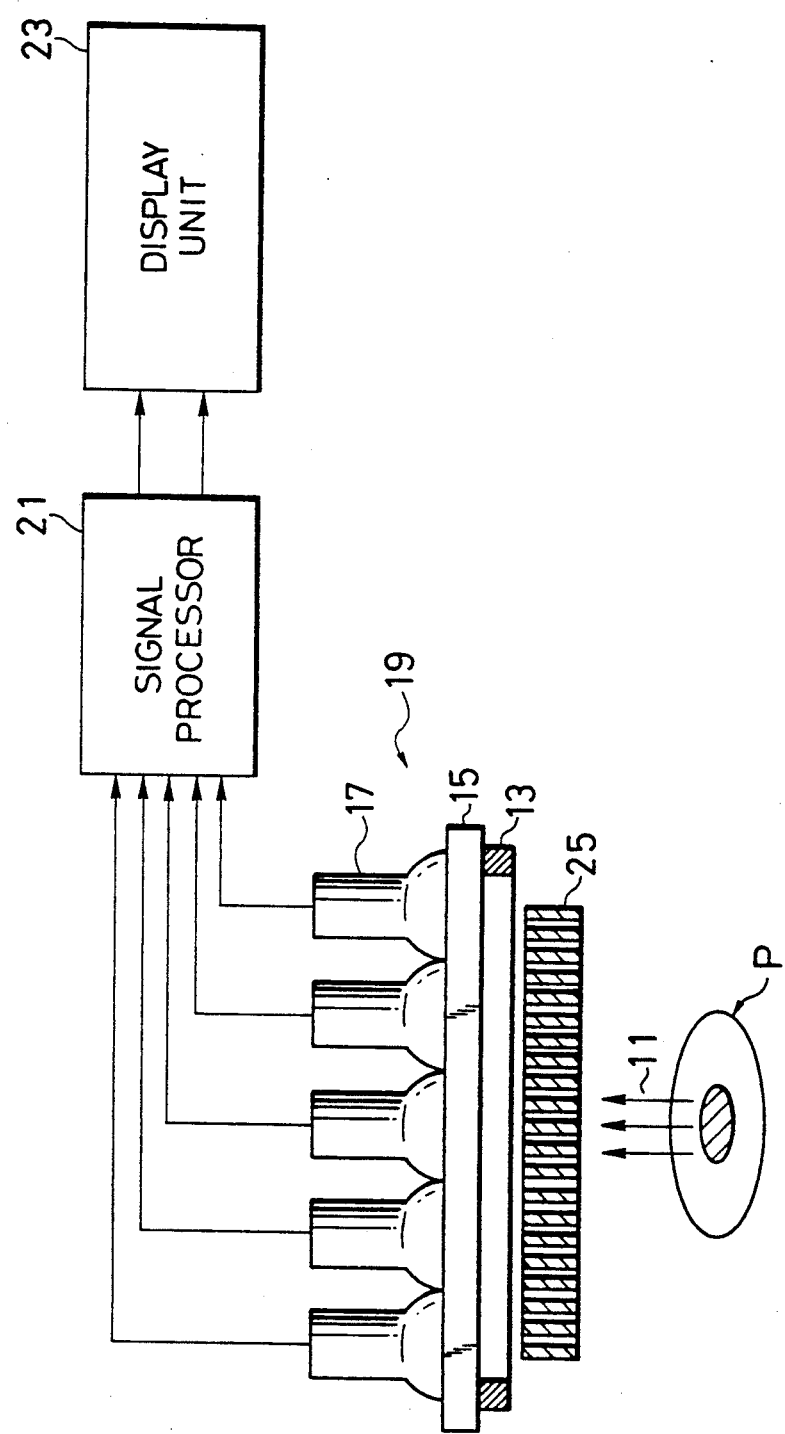
FIG. 1 is a view for explaining the principle of a gamma camera.
Figure 2A:
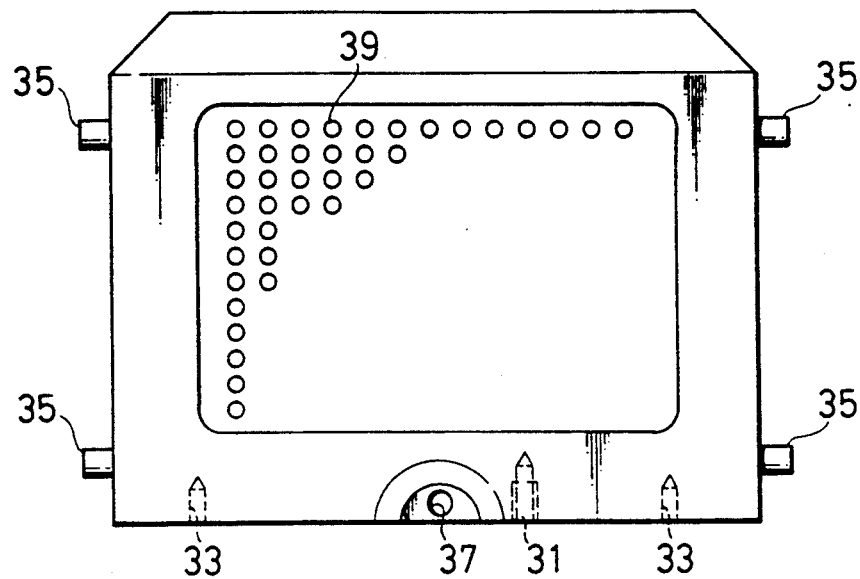
FIGS. 2A and 2B show a conventional collimator.
Figure 2B:
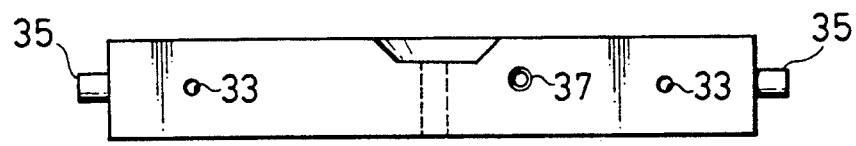
Figure 3:
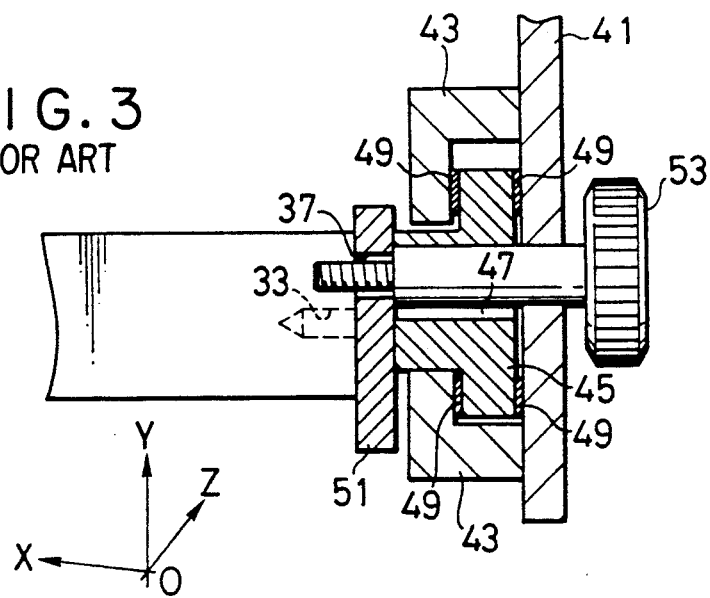
FIG. 3 shows a conventional connecting part for a holding device.
Figure 4:
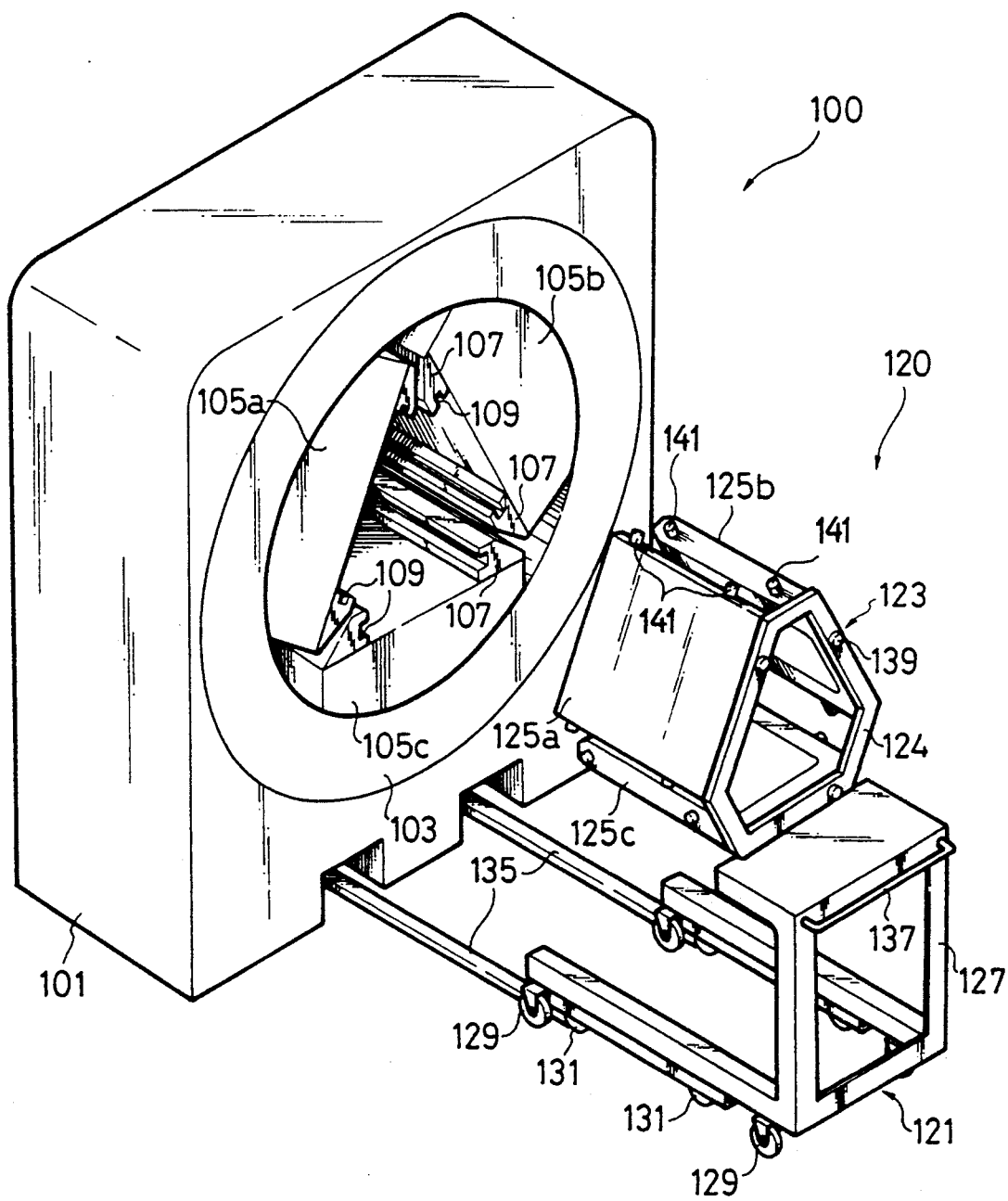
FIG. 4 is a perspective view of a scintillation camera of the first embodiment of the present invention.

FIG. 4 is a perspective illustration of a scintillation camera 100 of the first embodiment of the invention.

Figure 5:
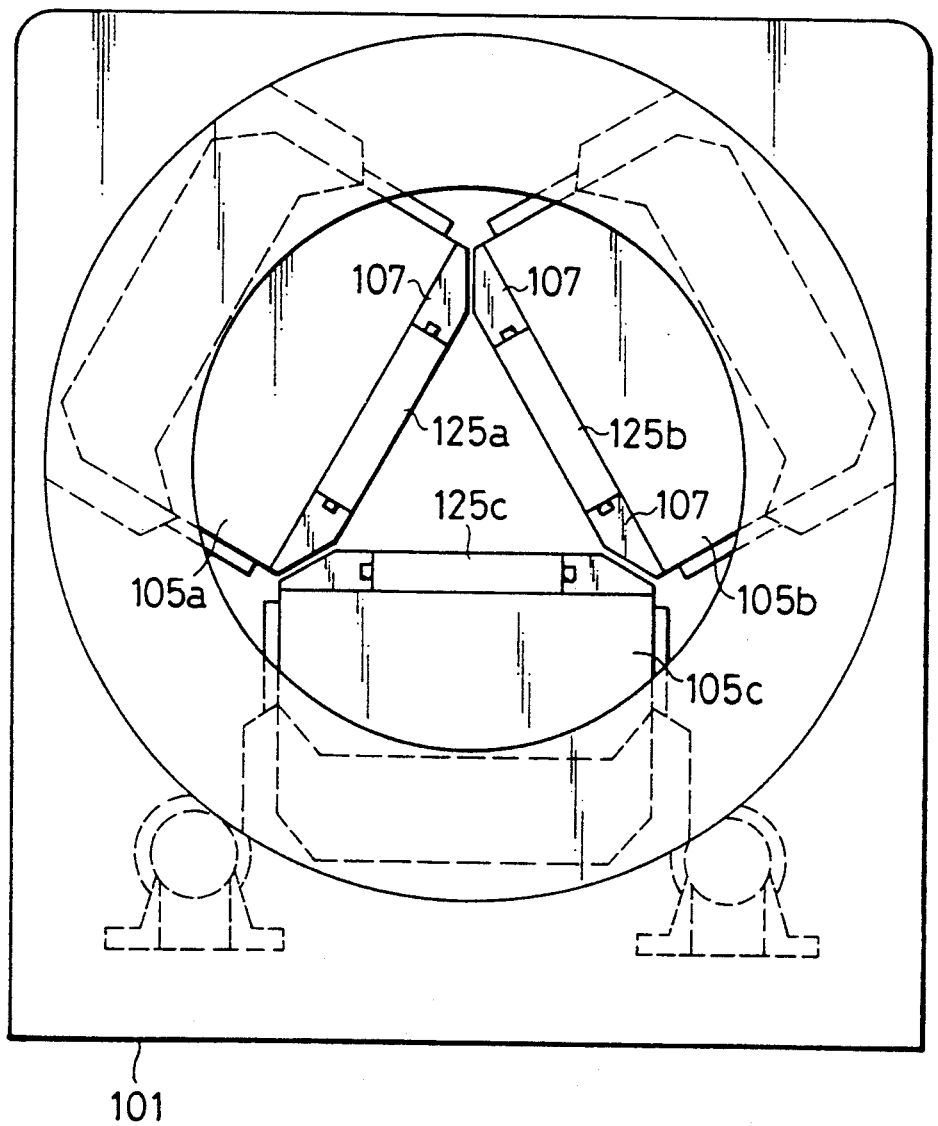
FIG. 5 is a front view of a gantry for the scintillation camera shown in FIG. 4.

As shown in FIG. 4 and in more detail in FIG. 5, a gantry 101 is provided with a rotation system including a rotating ring 103 for changing angles at which tomographic image is radiographed, three detectors 105a, 105b, 105c attached to the rotating ring, movable in the radial direction, for inserting an object among them and radiographing this object, attaching sections 107 with guide grooves 109 for attaching collimators properly on the front surfaces of the detectors 105.

A collimator exchanger 120 comprising a carrier 121 with rails 135 and a holding device 123 for holding collimators 125a, 125b, 125c, is removably positioned at the front of the gantry.

The carrier 121 consists of a frame body 127 with a plurality of running wheels 129 for running on the floor, a plurality of guide wheels 131 for running on the guide rails 135 and a handle 137. The guide wheels 131 are attached to the frame body 127 at a position a little higher than the running wheel 129 so that the carrier runs on the floor only with the running wheels without the guide wheel touching the floor, and runs on the guide rails with the guide wheel without the running wheel touching the floor. The rails 135 are secured to the floor parallel to the attaching sections 109 for proper exchange of the collimators and extend with a suitable length from the gantry 101.

The holding device 123 including a holding section 124 of a substantially triangular shape frame is secured to the top of the frame body. The holding section 124 is provided with three attaching screws 139 for holding three collimators. Each of the three collimators is maintained so that all of a plurality of guide pins 141 mounted on the collimator 125 are properly engaged in the corresponding grooves 109 of the attaching section 107.

Figure 6A:
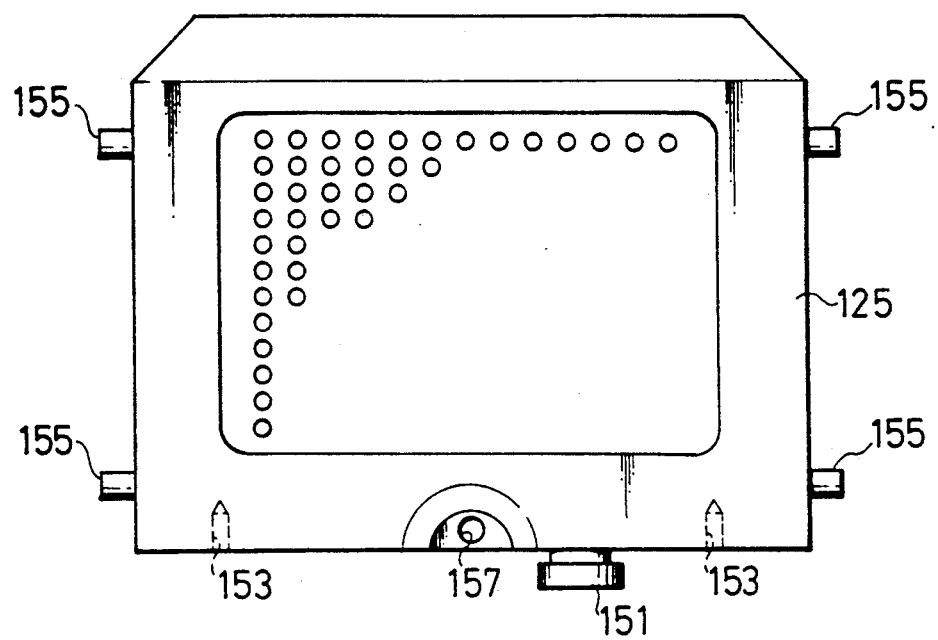
FIGS. 6A and 6B are a front view and a side view, respectively, of a collimator of the first embodiment of the invention.
Figure 6B:
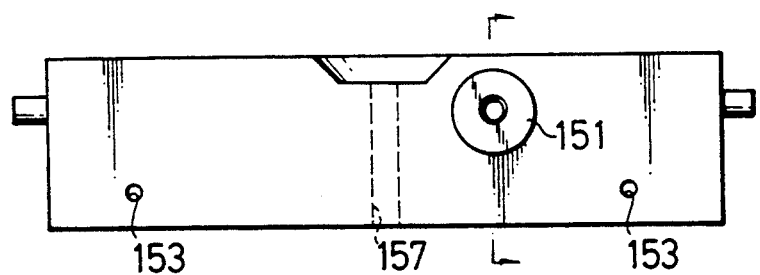

FIGS. 6A and 6B show a collimator 125 of the first embodiment. The collimator includes a connection part 151 with a spherical bearing and limiting pin holes 153. In the figures, guide pins 155 are used to engage the grooves 109 of the attaching section 107, a through hole 157 is used to secure the collimators 125 to the attaching section 107 with a screw (not shown) after complete insertion.

Figure 7:
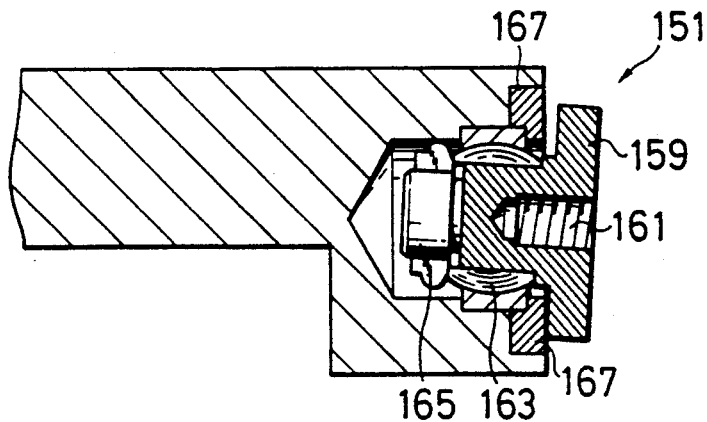
FIG. 7 is a sectional view of a connecting means of the first embodiment of the invention.

FIG. 7 is a detailed sectional view of a connected part 151 of the collimator. The connection part 151, as shown in FIG. 7, comprises a boss 159 with a screw hole 161 in the top for attaching to the holding section 124 and a male screw on the tail; a spherical bearing 163 for permitting the collimator 125 to swing in any direction; a nut 165 engaged with the male screw for securing the bearing 163 to the boss 159; and a securing member 167 for securing the bearing to a front end surface of the collimator.

Figure 8A:
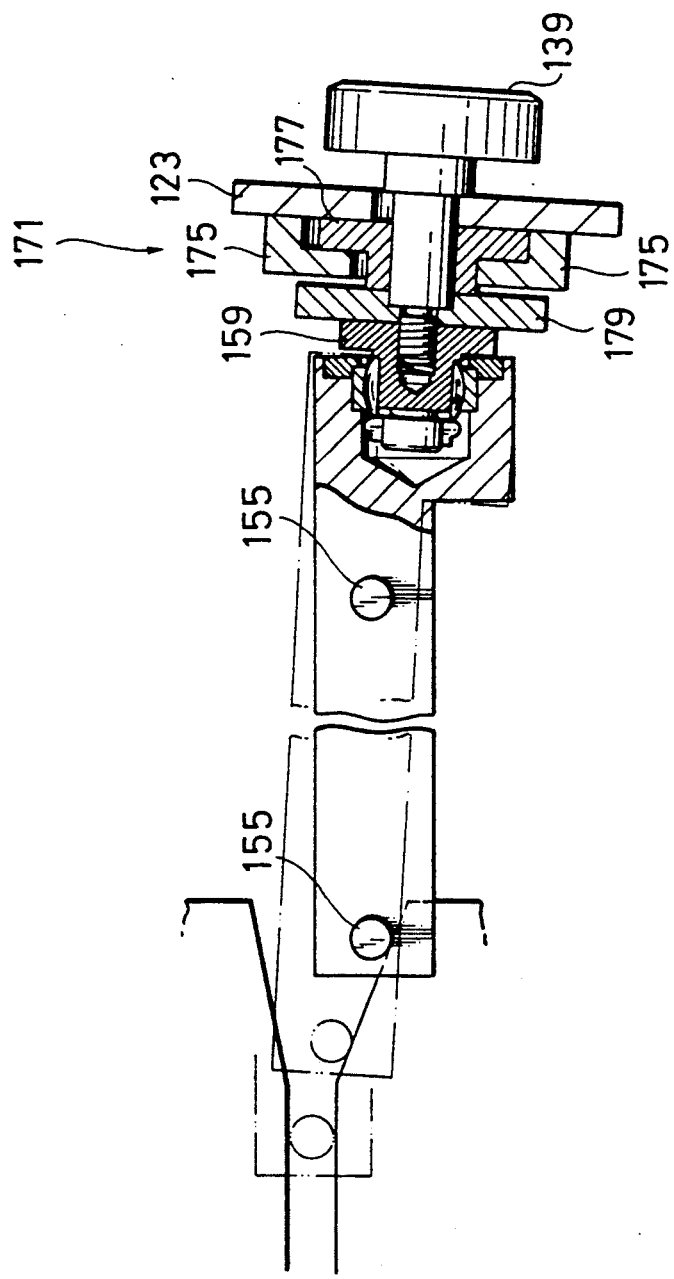
FIG. 8A is a side sectional view of the holding device of the first embodiment of the invention.

FIGS. 8A and 8B show a detailed sectional view of a holding means 171 of the holding device 123 and a limiting means 173 for limiting the swinging range of the collimator 125. The holding means 171 comprises, as shown in the figures, a first member 175 consisting of four blocks which are secured to the holding section 123; a second member 177 having a through hole and sliding parts joined to the first member 175 which is attached to the attaching section in the manner illustrated in FIG. 8C; a flat member 179 for attaching to the boss 159; and an attaching screw 139 for attaching the collimator to the holding section. The limiting means 173 comprises a limiting pin 181 secured to the flat member and a pin hole 183 for engaging the limiting pin. The detailed relationship of the pin 181 and the pin holes 183 are explained in FIGS. 9A, 9B, 10A, 10B, 11A and 11B. The relation between limiting pins 181 and the pin holes 183 differs according to the location at which the collimator is attached because the action of the force against the pins and the pin holes caused by gravitation differs according to attitude of the collimator, as seen in FIG. 4.

Figure 9A:
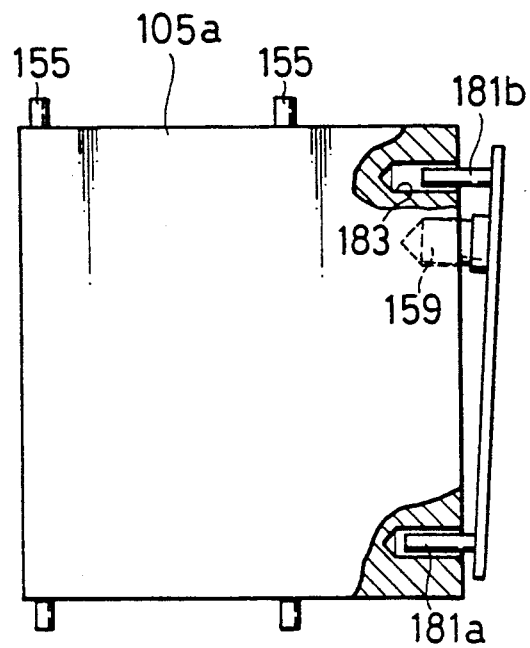
FIGS. 9A, 10A and 11A show the relation between a limiting pin and a pin hole for various cases.
Figure 9B:
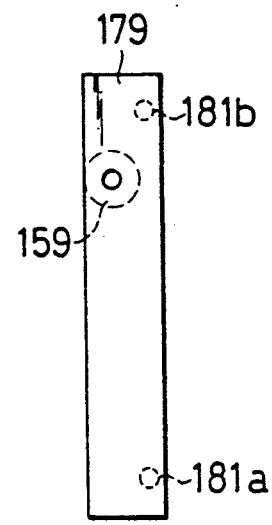
FIGS. 9B, 10B and 11B show the related locations of a limiting pin and an attaching screw.
Figure 10A:
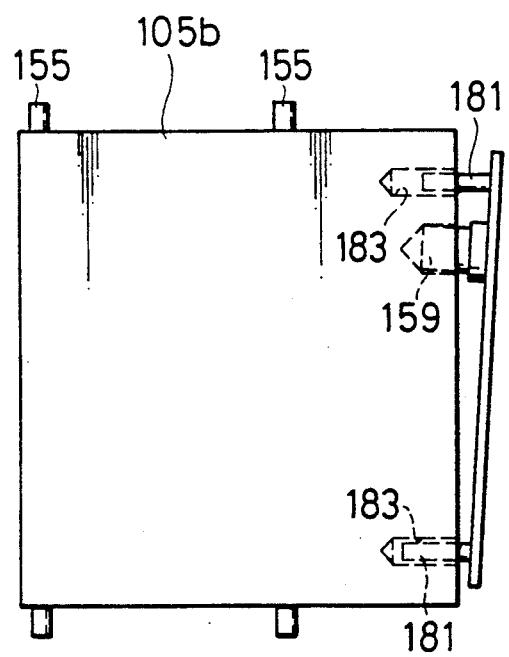
Figure 10B:
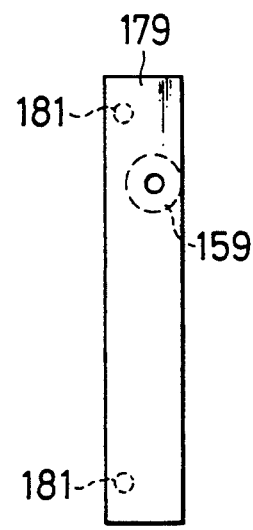
Figure 11A:
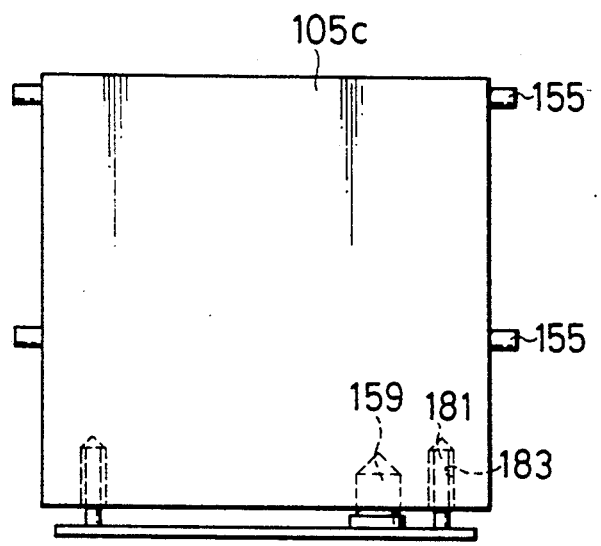
Figure 11B:
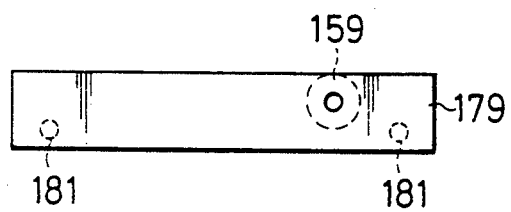

The collimator 105a located on the upper left side in FIG. 5 presses against the flat member at a lower and inner part, as seen in FIG. 9A and 9B, and the engagement between the pins and the pin holes is as shown in the figures. As seen in the figures, the lower limiting pin 181a is pressed and bent by the lower pin hole, and the upper limiting pin 181b is simply bent by the upper pin hole. The collimator 105b located on the upper right side in FIG. 5 is the same as the collimator 105a but the right and left side are reversed as seen in FIG. 10B. The collimator 105C located on the lower side in FIG. 5 presses against the flat member at a lower part, and the engagement of the pin and pin holes is as shown in FIGS. 11A and 11B. As seen in the figures, both lower pins are pressed and bent together by the pin holes. The dimensions and properties of the pins and the pin holes differ according to their purpose.

In this embodiment, each collimator weighs about 30 kg, the pins are about 25 mm in length and 15 mm in diameter. The swinging range is preferably within an angle of less than 10 degrees and a supporting means, for example, the first member 175 and the second member 177 in this embodiment supports the collimators preferably movably within a range of 3 mm×3 mm in two directions. The collimators 105 are provided with guide pins on both side ends, as seen in FIGS. 4 and 8B, for easier and proper attachment of the collimators.

Figure 12:
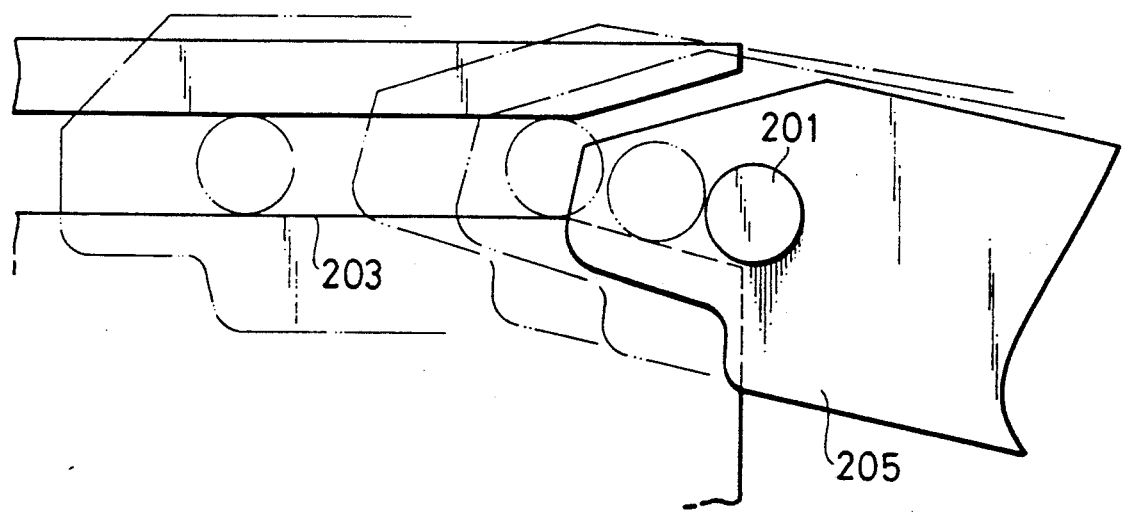
FIG. 12 shows an engaging process of a guide pin and a guide groove of an attaching section.

Each of the grooves 109 of the attaching section 107 has a tapered inlet for easy engagement of the corresponding guide pins 155, as seen in FIG. 8A. Both the collimators 125 and the attaching sections 107 are not always positioned at an exactly specified location. The attaching sections, for example, are stopped at a slightly shifted position or in a slanted posture. The collimators are sometimes maintained at a little higher or lower level or in a slanted posture FIG. 12 shows the process of insertion of a slanted and shifted collimator 205 into a groove 203. First, the leading guide pin 201 engages the entrance of the guide groove 203. Then, when the collimator 205 is pushed to the left, the guide pin 201 is slightly lifted and the collimator is rotated slightly counterclockwise until the pin 201 is at the same height as the groove 203 and the collimator 205 is parallel to the groove.

The step for attaching the collimators are as follows. First, each collimator is attached to the corresponding part of the flat member of the holding section with an attaching screw. Next the collimators are transported by the carrier along the guide rails until all the leading guide pins ride on the inlets of the guide grooves. All the leading guide pins can simultaneously ride on their corresponding inlets because each inlet has a wide entrance and the movable range of the leading guide pins is limited by the limiting means. Third, the collimators are inserted to smoothly move and swing up and down, and right and left as shown in FIG. 12 because the collimators are movably and swingably attached. FIG. 12 shows the process of insertion of the leading guide pins. Finally, insertions into the guide grooves are completed and all securing screws are set to secure the collimators to the attaching section.

The collimators are detached by reversing the attaching steps. As described above, the collimators of the invention are smoothly attached and detached even if the attaching section to the detectors are deviated from the specified positions, because the collimators are held movably and swingably. Therefore, a plurality of collimators are easily attached or detached simultaneously, which make exchanging operation of the collimators easy.

Figure 13:
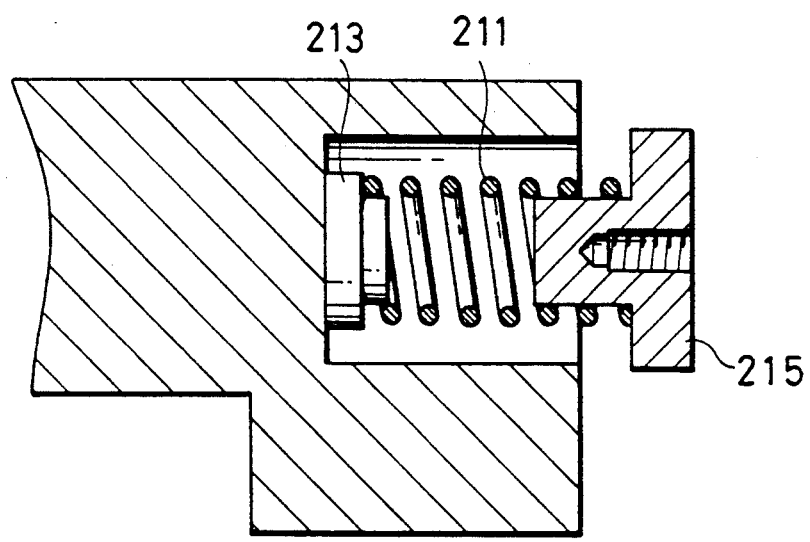
FIG. 13 is a sectional view of a connecting part of another embodiment of the invention.

FIG. 13 is another embodiment of the connecting means. The connecting means includes a spring 211 which permits the collimators to swing in any direction. Both ends of the spring are secured by a securing member 213 and a boss 215. This connecting means operates in the same manner as the before mentioned connecting means.

Figure 14:
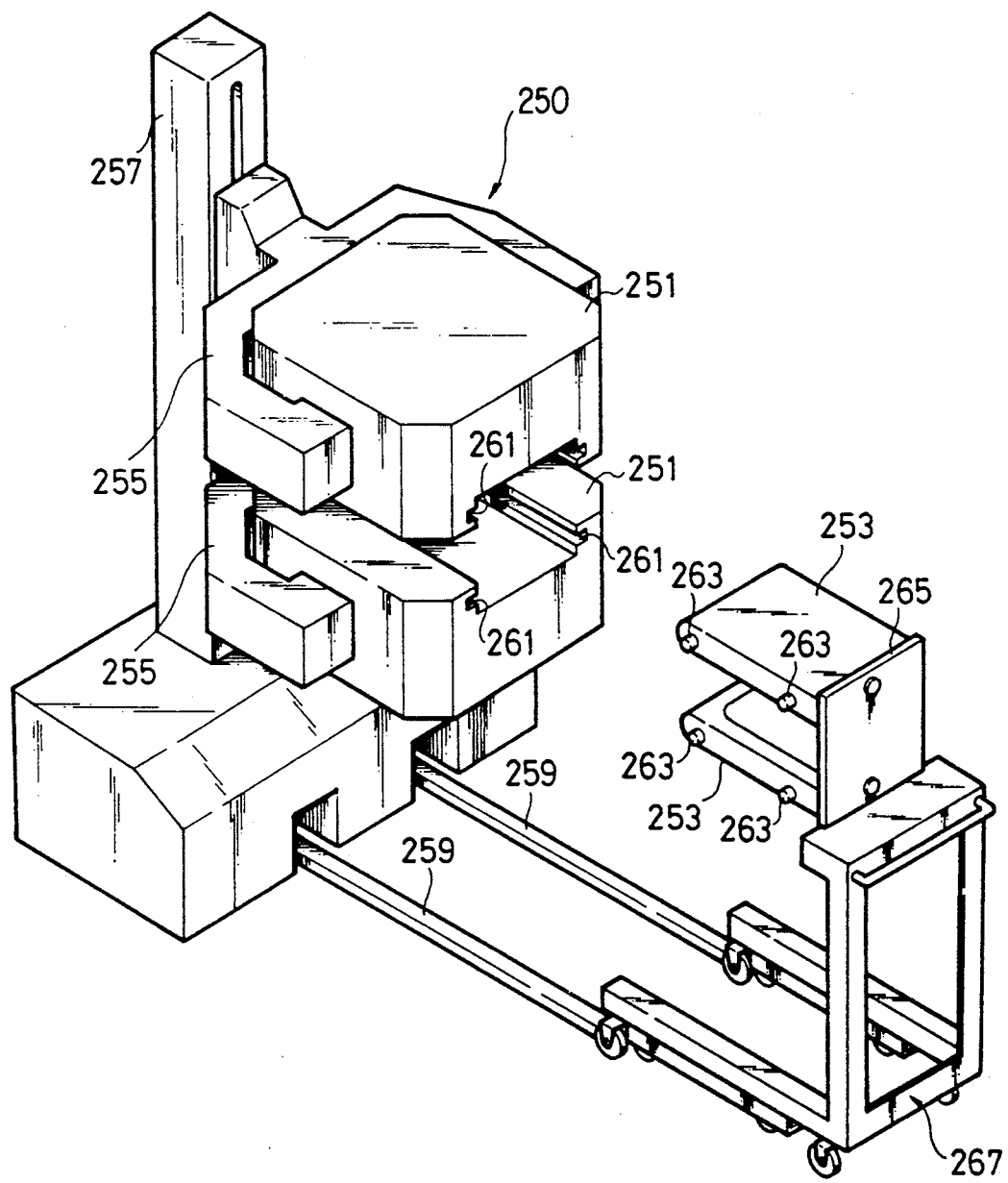
FIG. 14 is a perspective view of a scintillation camera of another embodiment of the invention.

FIG. 14 is an another embodiment of the present invention. This scintillation camera 250 includes two detectors 251 and two collimators 253. This embodiment relates to a stand type scintillation camera, i.e., the type in which detectors do not rotate. Bones of the human body and the like can be radiographed in such a case. In the figure, two detectors 251 are supported by a pair of U-shaped arm members 255 each of which moves up and down along a vertical member 257. This camera is provided with a collimator exchanger including the same connection part as in the camera of the first embodiment. A carrier 267 runs on rails 259 or on the floor for changing collimators 253. The collimators 253 are attached to a holding section 265 in the following manner: the carrier with the collimators for being attached thereto is moved towards the detectors 251 to engage front guide pins 263 with the inlet for guide grooves 261 and after so engaging, the carrier is again pushed in the same manner to install all guide pins 263 into the grooves 261. The inlet of the groove 261 is larger in width and height than other parts of the groove and has a slope for easier engagement of front pins 263, although this is not shown in detail in the figures. The holding section 265 holds the collimators in the manner as shown in FIGS. 8A and 8B. The attaching steps are performed in the manner as shown in FIG. 8C.

The main parts of this camera are the same as or analogous to that of the first embodiment, therefore a detailed explanation has been omitted.

Various modifications will become feasible for those skilled in the art after receiving the teaching of the present disclosure without departing from the scope thereof.

What is claimed is:

1. A scintillation camera, which comprises:
   a plurality of detectors mounted on the camera and arranged so as to provide an opening for allowing an object for examination such as a human being to be inserted into the opening and for radiographing a tomographic image;
   a plurality of collimators each attached to the front of the corresponding detectors for collimating X-rays radiating from the object for the examination; and
   an exchanger including a carrier and a holding device comprising a spherical bearing for holding said collimators in a swingable manner in any direction within a specified range.

2. A scintillation camera as claimed in claim 1, wherein:
   the holding device further comprises a pin and pinhole set for limiting the swinging range of the collimator.

3. A scintillation camera as claimed in claim 2, wherein:
   the swinging range is within an angle of less than 10 degrees.

4. A scintillation camera as claimed in claim 2, wherein:
   the holding device further comprises a sub-supporting means for supporting the collimators movably in a plane perpendicular to the collimator's surface.

5. A scintillation camera as claimed in claim 4, wherein:
   the sub-supporting means supports the collimators movably within a range of 3 mm×3 mm in two directions.

6. A scintillation camera as claimed in claim 2, wherein:
   the scintillation camera comprises three detectors equipped with a gantry in a form of an equilateral triangle.

7. A scintillation camera as claimed in claim 2, wherein:
   the scintillation camera comprises two detectors in parallel.

* * * * *